(12) United States Patent
Keenan et al.

(10) Patent No.: US 9,486,153 B2
(45) Date of Patent: *Nov. 8, 2016

(54) MEDICAL DEVICE SYSTEM HAVING AN IMPLANTED MEDICAL DEVICE AND AN EXTERNAL DEVICE

(71) Applicant: ANGEL MEDICAL SYSTEMS, INC., Fair Haven, NJ (US)

(72) Inventors: David Keenan, Tinton Falls, NJ (US); Michael Sasha John, Larchmont, NY (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/011,883

(22) Filed: Feb. 1, 2016

(65) Prior Publication Data

US 2016/0143533 A1 May 26, 2016

Related U.S. Application Data

(60) Continuation of application No. 14/313,251, filed on Jun. 24, 2014, now Pat. No. 9,326,696, which is a division of application No. 12/817,506, filed on Jun. 17, 2010, now Pat. No. 8,855,782.

(51) Int. Cl.
*A61N 1/00* (2006.01)
*A61B 5/0432* (2006.01)
*A61B 5/00* (2006.01)
(Continued)

(52) U.S. Cl.
CPC ........... *A61B 5/0432* (2013.01); *A61B 5/0031* (2013.01); *A61B 5/055* (2013.01); *A61B 5/7221* (2013.01); *A61B 5/742* (2013.01); *A61N 1/37252* (2013.01); *G06F 19/3406* (2013.01); *G06F 19/3418* (2013.01); *A61B 2560/0271* (2013.01)

(58) Field of Classification Search
CPC A61B 5/0031; A61B 5/0432; A61B 5/7221; A61B 5/742; A61B 2560/0271; A61N 1/37252; G06F 19/3406; G06F 19/3418

See application file for complete search history.

(56) References Cited

U.S. PATENT DOCUMENTS 6,442,432 B2 8/2002 Lee
6,795,735 B2 9/2004 Esler
(Continued)

*Primary Examiner* — Mallika D Fairchild
(74) *Attorney, Agent, or Firm* — Rosenberg, Kleni & Lee

(57) ABSTRACT

Disclosed is a system having an implanted component and external component which are configured to provide a test of wireless communication in order to assess the success or failure of such communication and to store attributes related to such test in a memory log. To provide the communication test the implantable and external components can attempt wireless communication according to communication test parameters which relate to number of times to retry communication, duration of sending communication test signals, durations of waiting for communication test signals and the schedule of the communication tests. The schedule of tests may be period or may change over time in order to become more or less frequency according to a programmable schedule that may also decrease if the communication tests are successful and indicate patient compliance in keeping the external components close by. The communication tests can assist in determining if the patient is maintaining external components within a suggested proximity (e.g. 6 feet) of the patient and may assist to determine if transmission or reception difficulties are the source of communication failure. A physician programmer can provide for programming, conducting, summarizing and assessing the results of communication tests.

20 Claims, 10 Drawing Sheets

(51) Int. Cl.
  *A61B 5/055* (2006.01)
  *A61N 1/372* (2006.01)
  *G06F 19/00* (2011.01)

(56) References Cited

U.S. PATENT DOCUMENTS

| | | |
|---|---|---|
| 7,558,623 B2 | 7/2009 | Fischell et al. |
| 7,738,964 B2 | 6/2010 | Von Arx et al. |
| 7,825,794 B2 | 11/2010 | Janetis et al. |
| 7,941,224 B2 | 5/2011 | Greenberg et al. |
| 2006/0116744 A1* | 6/2006 | Von Arx .................. A61N 1/08 607/60 |
| 2008/0097548 A1* | 4/2008 | Greenberg ......... A61N 1/36046 607/54 |
| 2009/0040041 A1* | 2/2009 | Janetis .................. G01S 5/0027 340/539.13 |

* cited by examiner

Proximity Alerting Test

Detailed Log — 280

Time →

IMD: S A S S A
     A C A C C
     C K C K K
     K 5 K F 4

EXD: A A
     C C
     K K
     2 3

282

Summary Results:
A. Average IMD → EXD Time: 23 seconds
B. Average EXD → IMD Time: 6 seconds
C. Max IMD → EXD Time: 34 seconds
D. Max EXD → IMD Time: 9 seconds
E. # Misses IMD → EXD: 1
F. # Misses EXD → IMD: 0
G. Average Strength (IMD → EXD): 4.5
H. Average Strength (EXD → IMD): 2.5

284 Change Send Duration
286 Change Send Strength
288 Change # Send
290 Change aCK Wait Duration/#
292 Change Test Fail Operations
294 Change EXD ACI
296 Run Proximity Test Now / Set Home-Based Test Parameters/Schedule
298

FIG. 9

MEDICAL DEVICE SYSTEM HAVING AN IMPLANTED MEDICAL DEVICE AND AN EXTERNAL DEVICE

CROSS REFERENCE TO RELATED APPLICATIONS

This application is a Continuation of pending U.S. application Ser. No. 14/313,251, filed on 24 Jun. 2014, which is a divisional of pending U.S. application Ser. No. 12/817,506, filed 17 Jun. 2010 entitled "MEDICAL ACCESSORY PROXIMITY TESTING, DETECTION, AND ALERTING SYSTEM", now U.S. Pat. No. 8,855,782.

FIELD OF USE

This invention is in the field of medical device systems that monitor a patient's health, and in particular, implantable medical devices that communicate with an external device.

BACKGROUND OF THE INVENTION

New devices that monitor and treat disorders such as cardiac or neural disorders rely upon patient interaction. Patient interaction may occur when a patient decides to adjust the operation of the implanted device, such as to turn the device on or off or to make an adjustment to its parameters. Patient interaction may also occur when the implanted device is set to relay data or an alert signal to an external device which can occur when an abnormal cardiac or neural event is detected. The patient can then interact by pressing a button on the external device to acknowledge that the alert signal has been received and that appropriate action (calling 911) will be initiated.

Communication between internal (implanted medical device or "IMD") and external (external device or "EXD") components of a medical system usually communicate in two modes. In a first mode, near-field communication is used. This is a relatively low power mode in which the external and internal device are placed very close to each other (e.g. within 2-3 inches). In the case of a cardiac device, the EXD must be placed directly over the chest where the IMD resides so that information can be transmitted and received without using much power. In a second manner of communicating, a far-field mode is used. Far field communication can use an antenna of the IMD and can transmit signals over a limited distance, such as 6 feet.

In order for the IMD and EXD to communicate the external components must be within a specified range (e.g. 6 feet) so that the transmissions from the internal components can be obtained by the external components, and vice-versa. Failure of the patient to keep the EXD within this range can prevent the IMD and EXD from communicating successfully. This can be known as an "out of range (OOR) error." Various types of OOR errors can occur in response to a number of different OOR events. These OOR events may include, for example: the IMD not finding the external device, the implantable device only finding an external device that is not the primary EXD with which it is intended to communicate, or the EXD not finding an IMD. Another type of OOR event occurs if an IMD or EXD is able to reach the sister device, but the signal is very weak, indicating that the devices may be "almost" out of range. Yet another type of OOR event occurs if one of the devices is able to reach the other device, but the communication interruptions exceed a specified criterion, indicating that the devices may possibly be "almost" out of range or that electromagnetic interference may be present.

There is a need for a system that can mitigate the problems associated with OOR events.

SUMMARY OF THE INVENTION

An embodiment of the invention comprises an implantable medical device and an external device that communicate with one other. The implanted medical devices comprises a transceiver, a random access memory, and a processor coupled to the transceiver and the random access memory. The processor is configured to wirelessly transmit a plurality of proximity test signals as part of a proximity test. For each of the plurality of proximity test signals, the processor determines determine whether a response has been received from the external device within a certain time after sending the corresponding proximity signal. If the internal device does not receive acknowledgement within a certain period, the internal device will enter the time and other pertinent information in a proximity test log. The external device also maintains a proximity test log. If proximity test failures are consistently occurring, the internal device sends a notification signal that can enable the patient in whom the device is implanted to take remedial action.

BRIEF DESCRIPTION OF THE DRAWINGS

FIG. 9 is a display of a Proximity Test Results screen.

DETAILED DESCRIPTION OF THE INVENTION

In the Specification and Claims herein, "proximity failure" broadly means a condition in which an implanted medical device and an external device are unable to communicate with one another, regardless of the cause of the communication failure. Communication failures may be caused by factors such as the external device being too far away from the implanted device or electromagnetic interference.

Architecture

Figure 1:
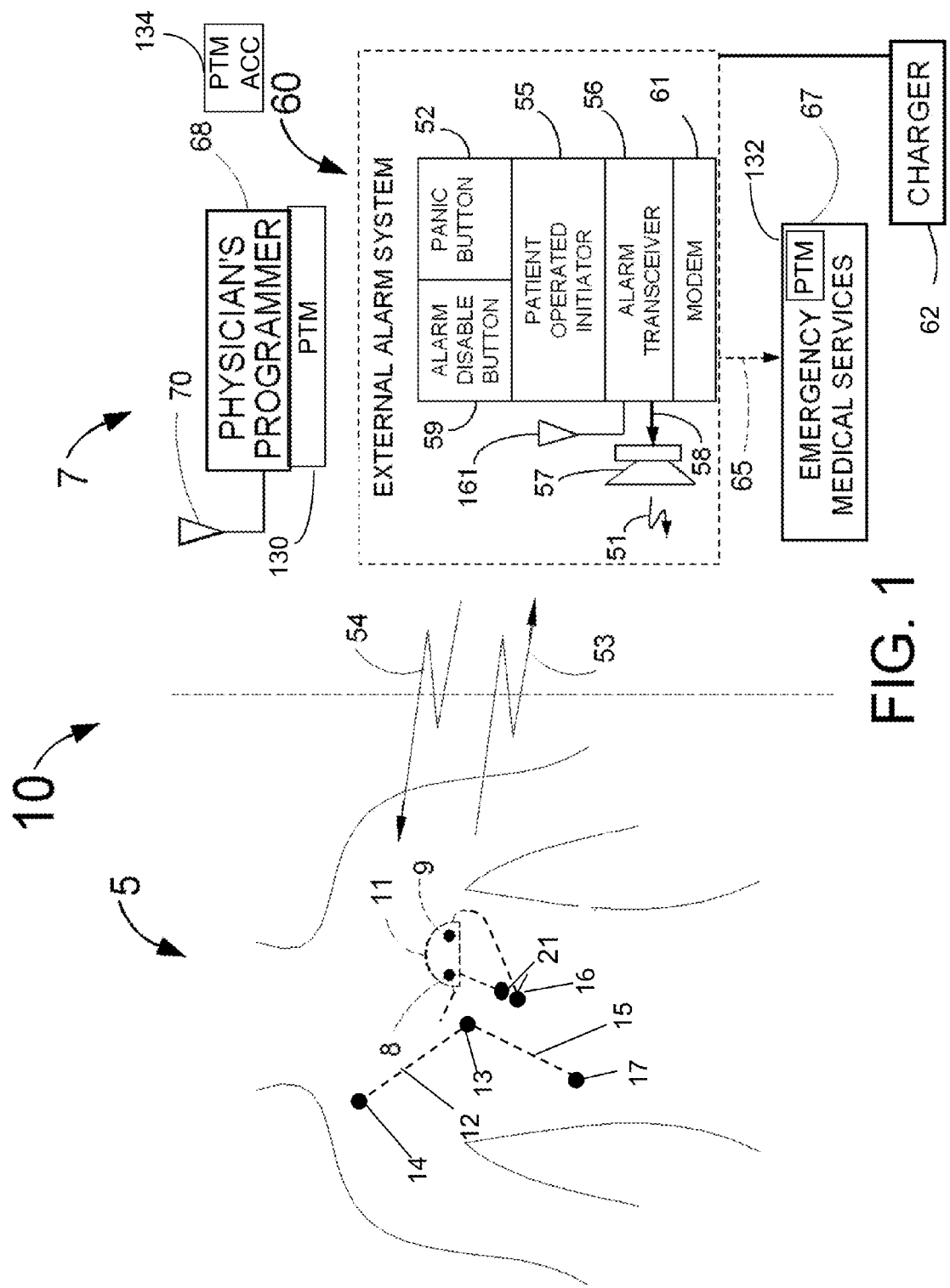
FIG. 1 illustrates a system for the detection of a cardiac event and for warning the patient that a medically relevant cardiac event is occurring.

FIG. 1 illustrates one embodiment of a system 10 comprising an implanted cardiac event detection device 5 and external equipment 7. The battery powered IMD 5 contains electronic circuitry that can detect a cardiac event such as an acute myocardial infarction or arrhythmia and warn the patient when the event, or a clinically relevant precursor, occurs. The IMD 5 can store the patient's electrocardiogram for later readout as well as send and receive wireless signals to, 53, and from, 54, the external equipment 7. The functioning of the IMD 5 will be explained in greater detail with the assistance of FIG. 2.

The IMD 5 receives electrical signals from intracardiac, subcutaneous or body surface leads 12 and 15, which, in the embodiment illustrated here, will be a clavicle and right side lead, respectively. Clavicle lead 12 comprises electrodes 13 and 14 with polarity hereafter defined as the difference potential measured between electrode 13 and electrode 14. Right side lead 15 comprises electrodes 13 and 6 with polarity hereafter defined as the potential at electrode 13 minus the potential at electrode 6. The electrode 13 is preferably disposed as close as possible to the sternum, in the fourth intercostal space on the right side of the body. The IMD 5 is housed in a metal case 11 that can serve as another electrode.

Many other embodiments of the present invention are possible. In one alternative embodiment, a lead is implanted within the heart, and the detection method of the present invention may be applied to signals received through that lead. In another alternative embodiment, subcutaneous electrodes in the following areas are used to form three separate leads: (1) the left precordial area (corresponding to lead V2 of the conventional 12 lead ECG); (2) the upper left pectoral region; and (3) the lowest portion on the left ribcage on the midaxillary line.

Also, as will be described more fully below, the present invention may be used in conjunction with an implantable cardioverter/defibrillator, a pacemaker or biventricular pacemaker (cardiac resynchronization therapy devices), or different types of implantable monitors (such as an implantable ventricular chamber pressure sensor or temperature sensor, neurostimulator, vagal stimulator, or insulin pump). In this case, an intracardiac lead 21, for example placed in the RV apex with the IMD housing 11 serving as the reference potential, may provide electrical signals for analysis. Extracardiac leads could also be employed.

According to one embodiment of the present invention, if the IMD 5 is used in conjunction with any of the above mentioned therapeutic devices, alarm data (associated with the present invention's detection scheme) is sent from the IMD 5 through a service such as St. Jude Merlin.net or Medtronic Carelink. The service, rather than the IMD 5, in turn notifies the patient that he/she needs to seek treatment. According to this possible implementation, the IMD 5 does not require an internal alarm, thereby potentially decreasing its size. For example, the size of a battery and motor necessary to provide a vibration alarm may be much larger than that needed to provide a sonic alarm, and this may cause the medical device to be relatively large.

FIG. 1 also shows the external equipment 7 that consists of a physician's programmer 68 having an antenna 70, and an external alarm system (or EXD) 60 including a charger 62. The external equipment 7 provides means to interact with the IMD 5. These interactions include, but are not limited to, programming the IMD 5, retrieving data collected by the IMD 5 and handling alarms generated by the IMD 5.

In FIG. 1, the external alarm system 60 has a patient operated initiator 55, an alarm disable button 59, a panic button 52, an alarm transceiver 56, an alarm speaker 57 and an antenna 161. It can also communicate with emergency medical services 67 via the modem 165 over the communication link 65. If a cardiac event is detected by the IMD 5, an alarm message is sent by a wireless signal 53 to the alarm transceiver 56 which receives this signal via the antenna 161. When the alarm signal is received by the alarm transceiver 56 a signal 58 is sent to the loudspeaker 57. The signal 58 will cause the loudspeaker to emit an external alarm signal 51 to warn the patient that an event has occurred. Examples of external alarm signals 51 include a periodic buzzing, a sequence of tones and/or a speech message that instructs the patient as to what actions should be taken. Furthermore, the alarm transceiver 56 can, depending upon the nature of the signal 53, send an outgoing signal over the link 65 to contact emergency medical services 67. The EXD 60 may also have a display screen for displaying messages related to system operation and inter-device communication (e.g. communication between the EXD and a remote medical station) or messages related to alarm testing (e.g., "2 alarm proximity tests have failed-press green button to continue", "See your doctor", "Go to ER") and may also contain colored LED's which indicate the occurrence of different types of events. When the detection of an acute myocardial infarction is the cause of the alarm, the alarm transceiver 56 could automatically notify emergency medical services 67 that a heart attack has occurred and an ambulance could be sent to treat the patient and to bring him to a hospital emergency room.

If the remote communication with emergency medical services 67 is enabled and a cardiac event alarm is sent within the signal from the IMD 53, the modem 61 will establish the data communications link 65 over which a message will be transmitted to the emergency medical services 67. The message sent over the link 65 may include any or all of the following information: (1) a specific patient is having an acute myocardial infarction or other medically relevant event, (2) the patient's name, address and a brief medical history, (3) a map and/or directions to where the patient is located, (4) the patient's stored electrogram including baseline electrogram data and the specific electrogram segment that generated the alarm (5) continuous real time electrogram data, and (6) a prescription written by the patient's personal physician as to the type and amount of drug to be administered to the patient in the event of a heart attack. If an emergency room visit at a hospital is required, information can be transmitted to the hospital (when this is part of the emergency medical services 67) that the patient has had a cardiac event and should be in transit to the emergency room. In this manner the medical practitioners at the emergency room could be prepared for the patient's arrival. The information sent over the link 65 may also be sent to the patient's primary doctor directly or via forwarding by the emergency medical services 67. Information can also be sent over the link 65 if there are a selected number of proximity test failures, although this is not an emergency situation, since it is a problem needing intervention. For example, if the patient is repeatedly failing their proximity tests then a medical technician can call the patient to determine why this is occurring. Proximity test results can be sent at the end of every day or every week or when the EXD 60 receives a request from the remote station, rather than after every proximity test is done. Further, the EXD 60 can be programmably configured to perform actions such as alerting the patient or sending proximity tests results to a remote station based upon test results, such as procuring a specified number of failures or if an excess have occurred within an certain amount of time.

The communications link 65 can be either a wired or wireless telephone connection that allows the alarm transceiver 56 to call out to emergency medical services 67. The typical external alarm system 60 might be built into a Pocket PC or Palm Pilot PDA where the alarm transceiver 56 and modem 61 are built into cards having a standardized interface such as compact flash cards, PCMCIA cards, multimedia, memory stick or secure digital (SD) cards. The modem 61 can be a wireless modem such as the Sierra AirCard 300 or the modem 61 may be a wired modem that connects to a standard telephone line. The modem 61 can also be integrated into the alarm transceiver 56.

The purpose of the patient operated initiator 55 is to give the patient the capability to initiate transmission of the most recently captured electrogram segment from the IMD 5 to the external alarm system 60. This will enable the electrogram segment to be displayed for a medical practitioner. The patient operated initiator button can be used in conjunction with a menu LCD display which will allow the patient to navigate through various menus relating to different device operations.

Once an internal and/or external alarm signal has been initiated, depressing the alarm disable button 59 will ACKnowledge the patient's awareness of the alarm and turn off the internal alarm signal generated within the IMD 5 and/or the external alarm signal 51 played through the speaker 57. If the alarm disable button 59 is not used by the patient to indicate acknowledgement and awareness of a SEE DOCTOR alert, an EMERGENCY alarm, or a proximity test requiring a response, it is envisioned that the internal and/or external alarm signals would stop after a time period (an initial alarm-on period) that would be adjustable through the programmer 68.

For EMERGENCY alarms, to help prevent a patient from ignoring or sleeping through the alarm signals generated during the initial alarm-on period, a reminder alarm signal might be turned on periodically during a follow-on periodic reminder time period. This periodic reminder time is typically much longer than the initial alarm-on period. The periodic reminder time period would usually be 3 to 5 hours because after 3 to 5 hours the patient's advantage from being alerted to seek medical attention for a severe cardiac event, like an AMI, is mostly lost. It is also envisioned that the periodic reminder time period could also be programmable through the programmer 68 to be as short as 5 minutes or even continue indefinitely until the patient acknowledges the alarm signal with the button 59 or the programmer 68 is used to interact with the IMD 5.

The IMD 5, the physicians programmer 68, the EXD 60, and emergency medical services 67 each have proximity testing module (PTM) which collaborate with the programmable parameter modules 477, 66, 130, 132, respectively. The PTM/Prog Parameter modules 477, 66, 130, 132 enable various components of the system to interact during proximity testing operations. The system may also contain a PTM accessory 134 which may be realized as a watch, pendant, or other wearable device. The EXD 60 may be programmed to perform some, or all, of its proximity checks by communicating with the PTM accessory 134 rather than with the IMD 5. Using the PTM accessory 134 rather than the IMD 5 during at least a portion of the proximity tests decreases usage of the IMD 5 battery 22. Additionally, in order to increase compliance of keeping the EXD 60 near the IMD 5, the EXD 60 may be realized as a wearable device such as a watch or pendant rather than a pager. In one preferred embodiment the medical monitoring and alerting system contains both an implanted device 5 and an external device 60 and at least the IMD 5 is configured with a proximity test module 477.

Figure 2:
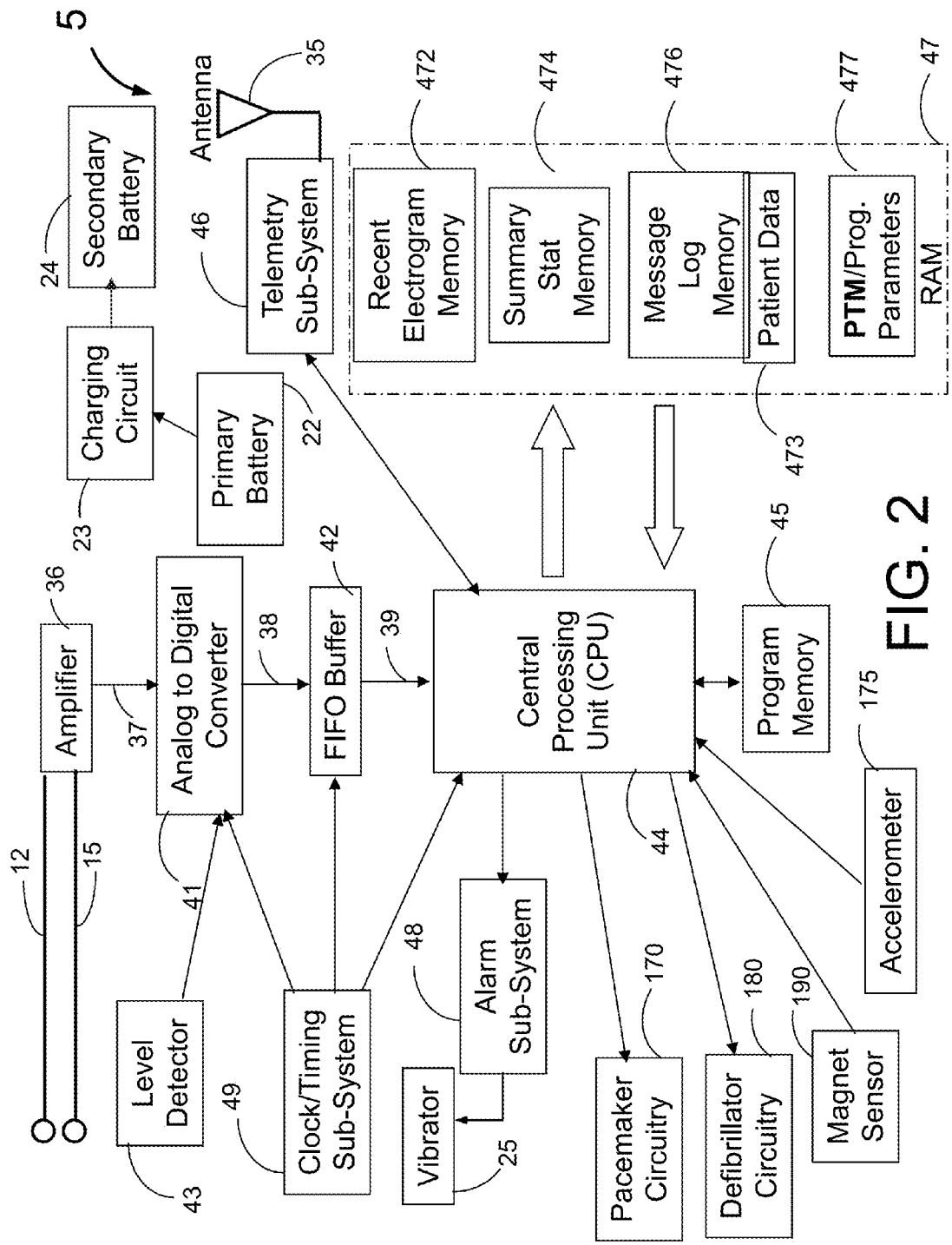
FIG. 2 is a block diagram of an IMD.

FIG. 2 is a block diagram of the IMD 5 with primary battery 22 and a secondary battery 24. The secondary battery 24 is typically a rechargeable battery of smaller capacity but higher current or voltage output than the primary battery 22 and is used by short duration, high output components of the IMD 5 like the RF chipset in the telemetry sub-system 46 or the vibrator 25 attached to the alarm sub-system 48. According to a dual battery configuration, the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The pairs of wires corresponding to leads 12 and 15 respectively connect to the amplifier 36, which is a multichannel or differential amplifier. The amplified electrocardiogram signals 37 from the amplifier 36 are then converted to digital signals 38 by the analog-to-digital converter 41, which preferably samples at a rate of at least 200 Hz. The digital electrocardiogram signals 38 are buffered in the First-In-First-Out (FIFO) memory 42. Processor means shown in FIG. 2 as the central processing unit (CPU) 44 coupled to memory means shown in FIG. 2 as the Random Access Memory (RAM) 47 can perform instructions stored in the program memory 45 that implement the flowchart shown in FIG. 4.

A level detector 43 is coupled to the analog to digital converter 41. The level detector 43 detects whether a patient's torso is upright or supine and also, if the torso is supine, the extent of its rotation with respect to the earth (e.g. patient is lying flat on his/her back, lying on his/her right side or left side.) There are many types of MEMS based level detectors which can also serve as inclinometers, accelerometers, and general detectors for motion and force.

Additional sensors may communicate with the IMD 5 wirelessly through the telemetry sub-system 46. The data from these leads may correspond to digitized electrocardiogram signals (that have been processed by a remote subcutaneous device).

The operation of most of the components in FIG. 2 is further described in U.S. patent application publication number 2004/0215092.

In a preferred embodiment of the present invention the RAM 47 includes specific memory locations to store sets of electrocardiogram segments. These memory locations are the recent electrocardiogram storage 472 that would store the last 2 to 10 minutes of recently recorded electrocardiogram segments so that the electrocardiogram data occurring just before the onset of a cardiac event can be reviewed at a later time by the patient's physician using the physician's programmer 68 of FIG. 1. For example, the recent electrocardiogram storage 472 might contain eight 10-second long electrocardiogram segments that were captured every 30 seconds over the last 4 minutes.

A summary statistics memory 474 would provide storage for summary information, such as running averages, of various cardiac waveform feature values. A message log memory 476 stores proximity log information as will be described with reference to blocks 112 and 114 of FIG. 4. Memory 473 stores patient specific information (e.g. patient name, date of birth). Memory 477 stores programming parameters and proximity test modules that control various operations associated with the proximity tests and storage of proximity test results in the proximity log 476 of the present invention.

The telemetry sub-system 46 with antenna 35 provides the IMD 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the IMD 5. It is also envisioned that standard wireless protocols such as Bluetooth and 802.11a or 802.11b might be used to allow communication with a wider group of peripheral devices.

Figure 3:
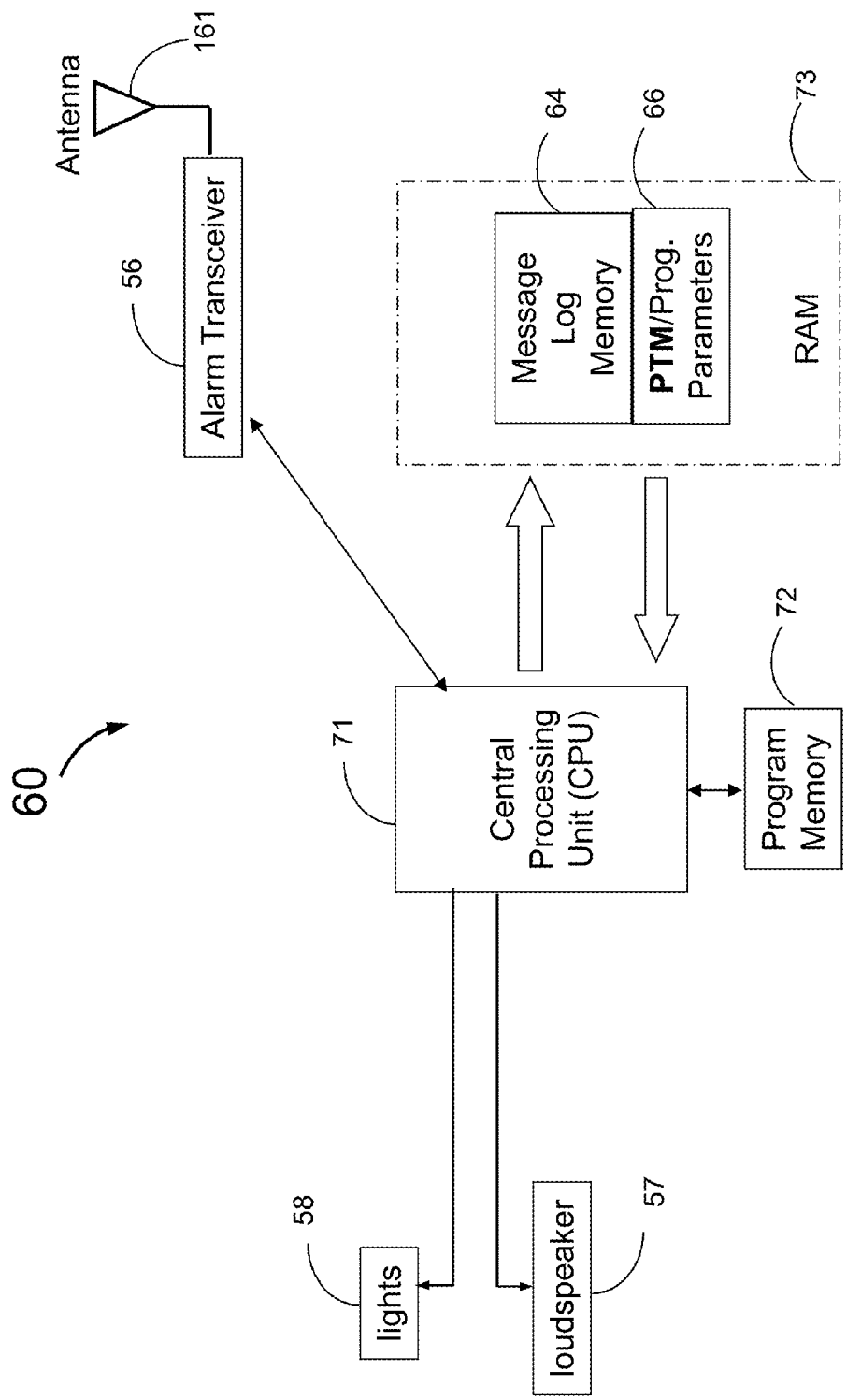
FIG. 3 is a block diagram of an EXD that communicates with the internal device shown in FIG. 2.

FIG. 3 is a block diagram of the EXD 60. Memory 66 stores proximity test module (PTM) operations which are defined to perform proximity tests and programming parameters that control various operations associated with the proximity log features of the present invention. A central processing unit (CPU) 71 is coupled to the alarm transceiver 56 which receives signals from the antenna 161, as was described with reference to FIG. 1. The CPU 71 is also coupled to a random access memory 73, which is subdivided into a message log memory 64 and a PMT/programming parameters memory 66. The CPU 71 is also coupled to the lights (and/or LCD display/colored LEDS) 58 and the loudspeaker 57. The CPU 71 implements the flowchart shown in FIG. 5 according to instructions stored in a program memory 72, which may be loaded in from the PTM/prog parameters memory 66. The CPU 71 interacts with the patients via patient operated buttons (52, 55, 59) which can be used to interact with the EXD 60, and indirectly with the IMD 5, during proximity tests. The CPU 71 may contain timing/clock circuitry which provides timing information needed for carrying out its operation.

Figure 4:
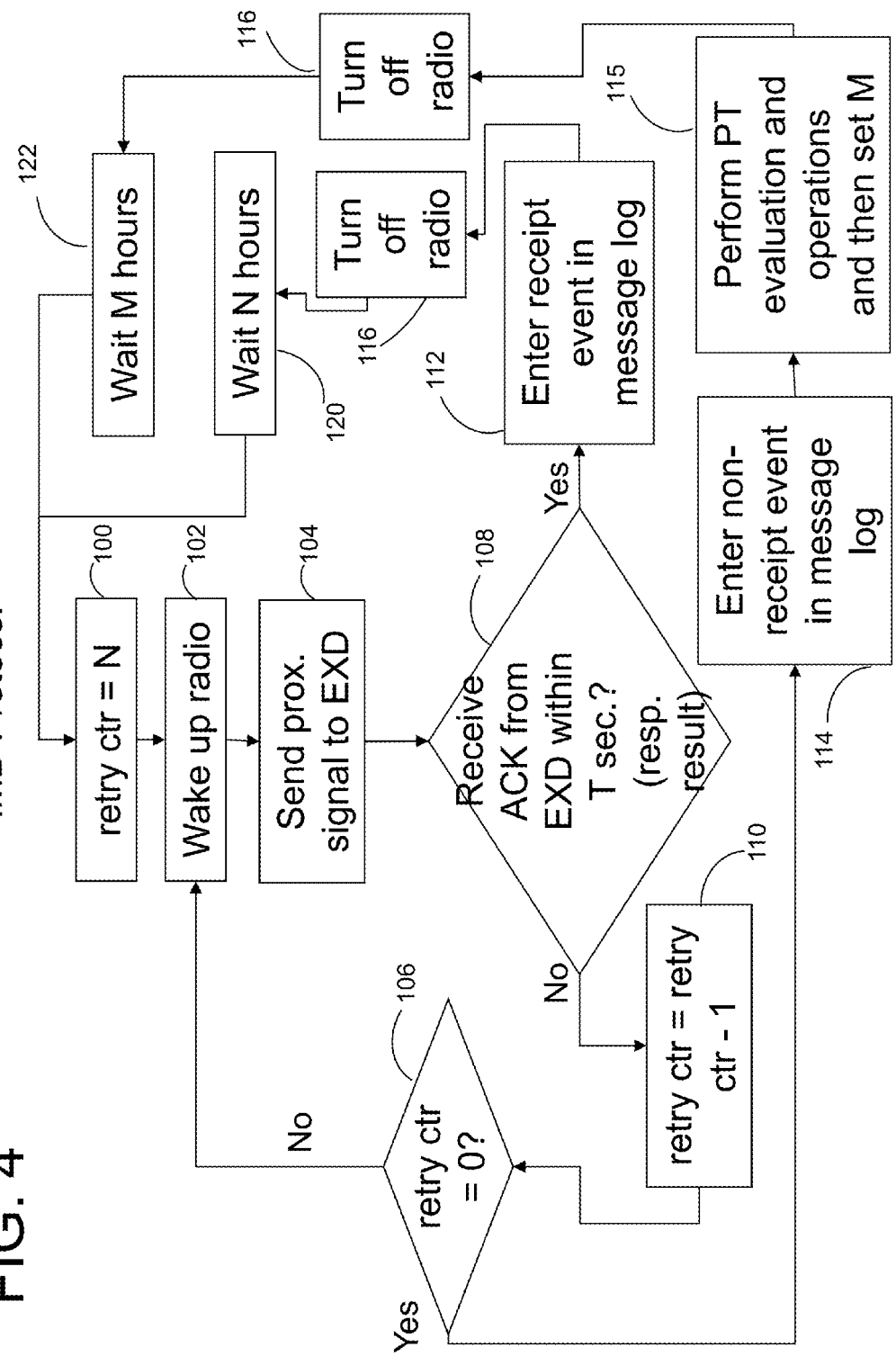
FIG. 4 is a flow chart of a proximity check communication method, implemented by the IMD, according to the present invention.

FIG. 4 is a flow chart of a proximity test method, implemented by the IMD 5, according to the present invention. In block 100, a retry counter is set to N. As will be further described below, the retry counter governs the number of attempts to contact the EXD 60 before declaring a proximity failure. In block 102, the IMD 5 "wakes up" the wireless communication circuitry (telemetry subsystem 46 in FIG. 2). In block 104, the telemetry subsystem 46 sends a proximity check signal to the EXD 60.

In block 108, the IMD 5 determines whether it has received an acknowledgement (ACK) from the EXD 60 within a predetermined amount of time, T seconds, where a preferred value of T is 600 ms. Reception of an ACK within this time is a positive proximity test result whereas lack of such reception is a negative proximity test result. If block 108 returns a positive result, control transfers to block 112, where the receipt of the ACK is written in a message log, whose format will be further described with reference to FIG. 6. In block 112, the IMD 5 can maintain its own message log in the message log memory 476 (see FIG. 2). From block 112, control transfers to block 120 (after turning off radio in step 116), which waits N hours before reinitiating the proximity check cycle, where preferred values of N are 6, 24, and 72. As will be described, when the patient first is implanted it may be important to check 4 times a day for 3-4 days to ensure the patient is keeping the EXD 60 nearby, which can decrease to once every day or 3 days thereafter. Alternatively, rather than being accomplished by the IMD, this can be mostly carried out using the PTM accessory 134, which can rely on its own circuitry and a method which may be implemented as just described. In some testing situations it doesn't matter whether the IMD 5 or the PTM accessory 134 conducts the test, such as when the goal is to make sure that the patient is keeping the EXD 60 nearby.

Returning to block 108, if an ACK has not been received from the EXD 60 within T sec., the control transfers to block 110, which decrements the retry counter. Control transfers to block 106, which applies a test to determine whether a proximity failure condition exists. In the preferred embodiment, the test is whether the retry counter is equal to 0, which would mean that N attempts to contact the EXD 60 have all resulted in failure. If that is the case, block 106 transfers control to block 114, which logs the non-receipt event in the message log 200 in FIG. 6. In step 115, the IMD 5 evaluates the history of events in the message log according to proximity test rules set up in the PTM/Prog parameters module 477 and determines if proximity failure-condition operations need to occur (e.g., if proximity tests have failed for the last week then alert the patient) as well as calculating the next value of M depending upon the PTM parameters. If the proximity tests have failed for more than a specified period the IMD 5 may provide an internal alert since it may be unable to communicate with the EXD 60. However, in a preferred embodiment, if the EXD 60 doesn't receive the cue to perform a proximity test during a specified period (e.g. 1 week) then it will alert the patient. It is preferable to have the EXD rather than IMD alert the patient in order to decrease usage of the IMD 5 battery 22. Control then transfers to block 122 (after turning off radio in step 116), which implements a M-hour delay before repeating the entire procedure starting at block 100.

Returning to block 106, if the retry counter is greater than 0, then block 106 transfers control to block 102, and another attempt is made to contact the EXD 60.

Figure 5:
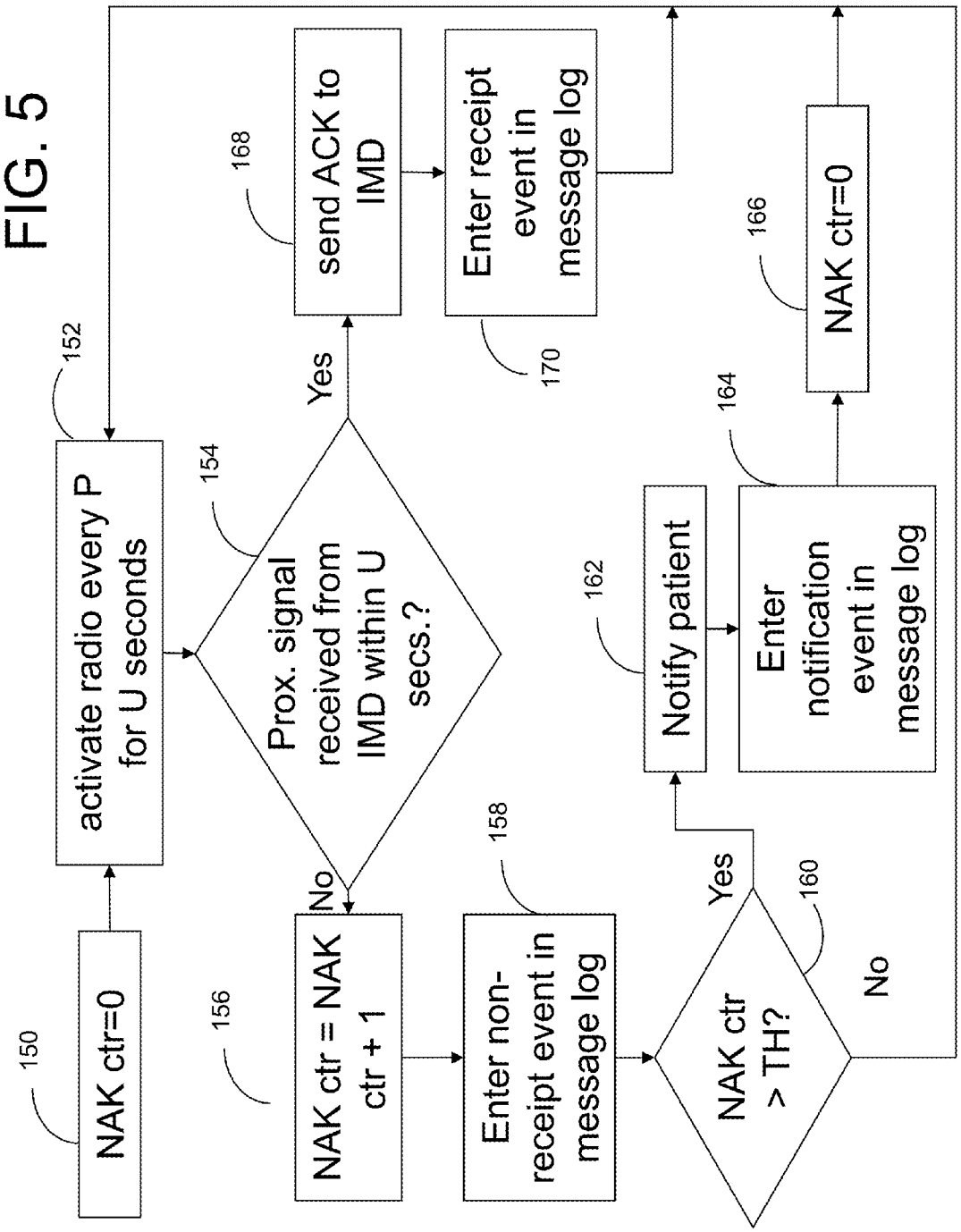
FIG. 5 is a flow chart of a proximity check communication method, implemented by the EXD, according to the present invention.

FIG. 5 is a flow chart of a proximity check test method, implemented by the EXD 60, according to the present invention. In block 150, a NAK counter is set to 0. As will be further described below, the NAK counter governs the number of attempts to receive a test message from the IMD 5 before detecting a proximity failure. In block 152, every P seconds the EXD 60 "wakes up" its radio (alarm transceiver 56 in FIG. 3) for U seconds. Preferred values for P and U are 90 and 3. With respect to proximity testing, in one embodiment, P can be set to provide a delay of 72 hours and U set at 60. In this instance the IMD 5 is also programmed to perform a proximity test every 3 days and it wakes up its transceiver 56 for some duration (e.g., a minute) in order to participate in the test with the EXD 60. In this case, in order to compensate for clock drift, the IMD 5 sends clock information along with its communication during the proximity test and the EXD 60 uses this information to adjust the next time at which it will perform the proximity test.

Block 154 determines whether the EXD 60 has received a proximity test signal from the IMD 5 within a predetermined amount of time, U seconds, where a preferred value of U is 3. If block 154 returns a positive result, control transfers to block 168, where the EXD 60 sends an ACK to the IMD 5. Control then transfers to block 170, which causes the EXD 60 to log the ACK send event into its message log, whose format will be further described with reference to FIG. 6. The EXD 60 maintains its own message log in the event log memory 64 (FIG. 3). From block 170, control transfers back to block 152 to restart the cycle.

Returning to block 154, if a proximity signal has not been received from the IMD 5 within U sec., the control transfers to block 156, which increments the NAK counter. Control transfers to block 158, which logs the non-receipt event in the message log of the EXD 60.

Control then transfers to block 160, which applies a criterion test as defined by the proximity test module/prog parameters 66 to determine whether a proximity failure condition exists. In the preferred embodiment, this test is whether the NAK ctr is above a threshold (TH). TH is a programmable value that may be adjusted, for example, in relation to M and N values (or ranges of M and N values) as defined in steps 120 and 122. If the NAK ctr is above TH, in block 162, the EXD 60 notifies the patient of the proximity failure by sending an audible signal through the loudspeaker 57 (FIG. 3) and/or activating lights/visual display 58 (FIG. 3). The EXD 60 is preferably programmable so that it may be further configured to also send this alert to a central station/medical practitioner. Alternatively, the alert is only sent to a remote location after the patient has been notified a selected number of times. Additionally, the NAK counter may be decremented by a value of 1 every R-hours in step 156, so that a patient alert is only generated if there are a specified number of communication errors within a specified period. Further, in an alternate embodiment, the patient can enter a condition (e.g. on an airplane) into the message log memory 64 of the EXD 60 in order to indicate the possible cause of the failure, so that patient alerting or proximity testing does not occur for a selected period.

In block 164, the alert notification event is entered into the message log of EXD 60. In block 166, the NAK counter is reset to 0, and the cycle is restarted in block 152.

According to an alternate embodiment, rather than the patient being notified according to block 162 that the NAK counter has passed a threshold value TH within step 160 (meaning too many proximity test signals from the IMD 5 have not been detected) the patient is alerted only when the EXD 60 reviews its message log and determines that the history of NAKs meets a criterion selected by the proximity test module of EXD 60. In other words, step 164 occurs directly after step 160, and then the message log is evaluated to determine whether patient notification is proper. If so, then step 162 is performed. Further, the proximity signal sent by the IMD 5 can also contain the time at which it received the last ACK from the EXD 60 so that the EXD 60 can determine if the IMD 5 received the ACK sent the last time step 168 occurred. In this manner the EXD 60 can keep track not only of its failures to receive signals sent from the IMD 5 but also failures of the IMD 5 to receive signals sent from the EXD 60.

Figure 6:
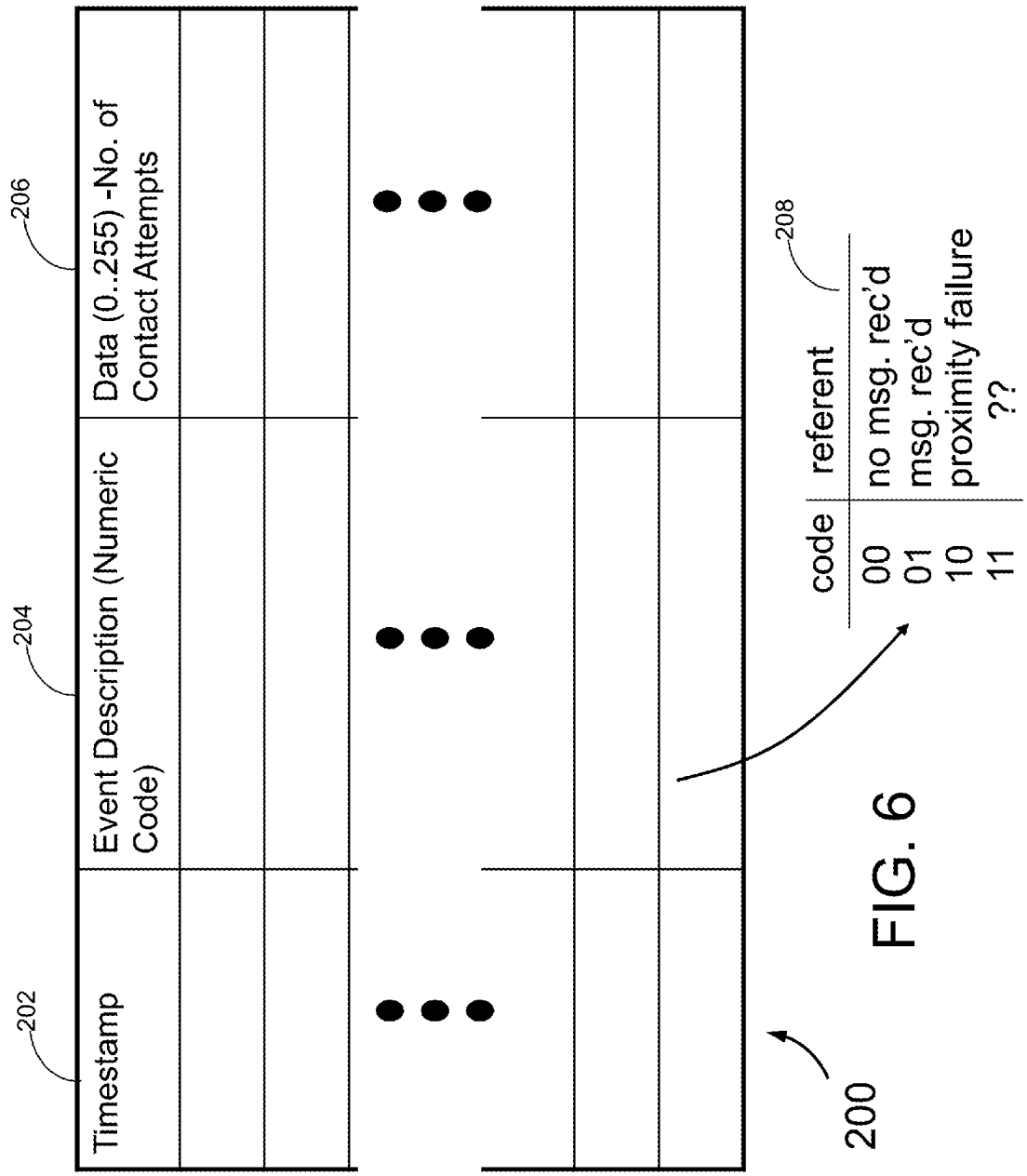
FIG. 6 is a diagram of a proximity log maintained by the IMD and EXD.

FIG. 6 is a diagram of a proximity log 200 maintained by the IMD 5 and EXD 60 in their proximity log memories 476 and 64, respectively. In this embodiment, the proximity log 200 is a table with multiple columns and one row for each logged event. The columns are a timestamp field 202, an event description field 204 and a data field. The timestamp field 202 is the date and time of an event or may be represented as ticks of a counter.

The event description field 204 is a two bit field that encodes the description of an event according to a coding scheme shown in table 208. Primary events are "no message received" and "message received." In a preferred proximity test embodiment, in the case of the IMD 5, a "message received" is an ACK from the EXD 60 (block 112 of FIG. 4). In the case of the EXD 60, a "message received" is the reception of a test message from the IMD 5 (block 170 of FIG. 5). The EXD 60 also logs proximity failure events (block 164 of FIG. 5) in the event description field.

The data field 206 is a 256 byte field that may include a variety of information), including the number of failed communication attempts in the case that no message is received by the IMD 5 or EXD 60 from the other device (e.g., as computed by "retry ctr" and "NAK-ctr" in the step 156 or 110 of FIGS. 4 and 5). The data field may also contain values related to the strength of the signal which was received, a proximity test paradigm identification number which can indicate the protocol that was used for the proximity test, and associated values which are set for the protocol.

Figure 7:
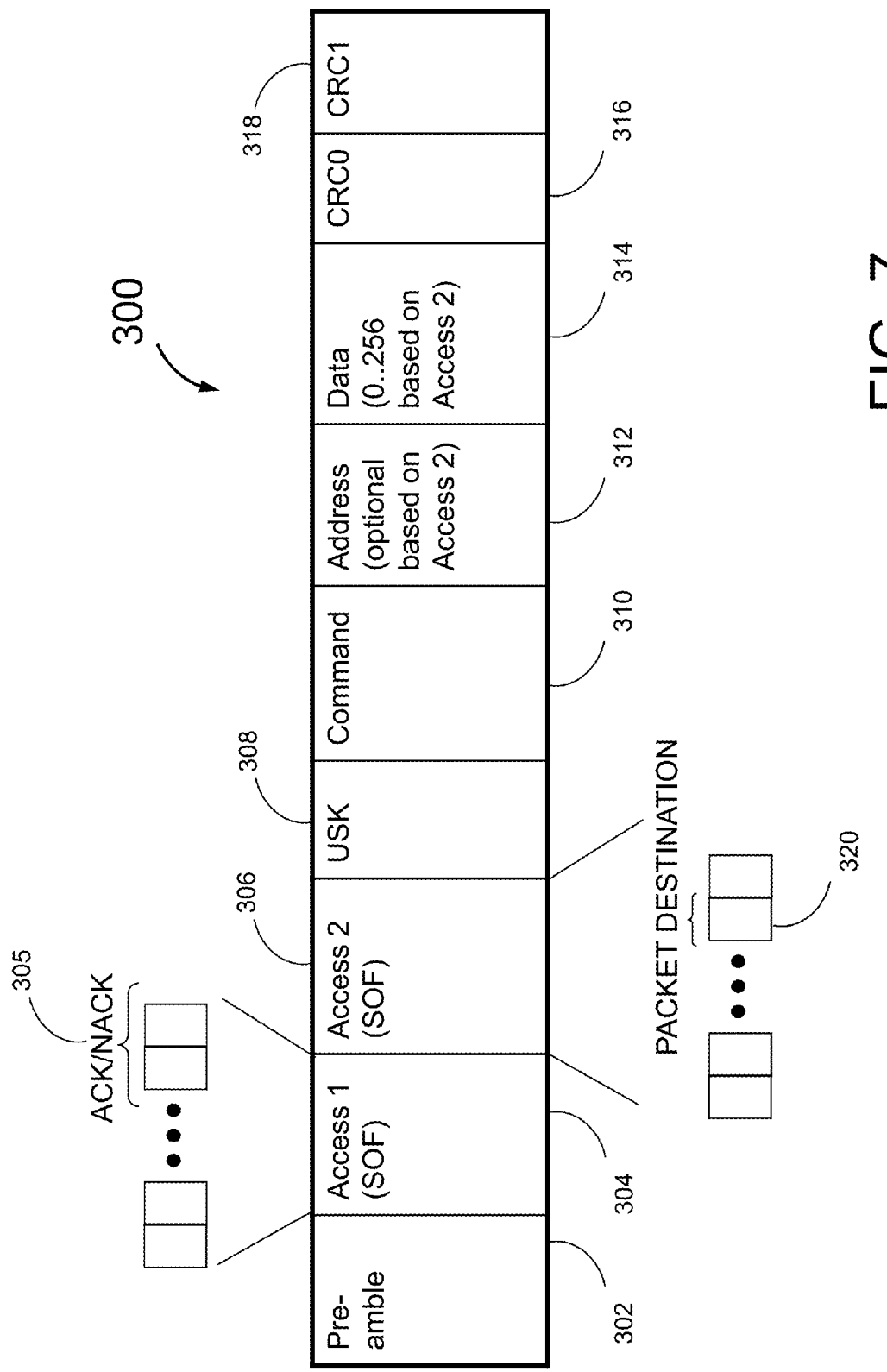
FIG. 7 is a diagram of the format of packets exchanged between the IMD and EXD.

FIG. 7 is a diagram of the format of packets (e.g. data packets) exchanged between the IMD 5 and EXD 60. In this example, a packet 300 comprises a preamble field 302, an "Access 1" field 304, and an "Access 2" field 306, a USK field 308, an optional address field 312, a data field 314, and two cyclical redundancy fields 316 and 318.

The preamble field 302 preferably comprises 6 bytes with a constant value of 0xAA. The "Access 1" field 304 is preferably one byte that provides a customer/access code to the host device (e.g. IMD 5 or EXD 60). Part of field 304 is a two bit sub-field 305 that stores ACK/NAK response information from the EXD 60 (see block 168 of FIG. 5 for the ACK response).

The "Access 2" field 306 is preferably a single byte that provides device specific access. A subfield 320 is a single bit that indicates the direction of the communication packet (e.g. a 0 indicates IMD 5 to EXD 60 transmission while a 1 indicates the reverse.

A USK field 308 is pseudo randomly generated by the EXD 60 for each communication session established. This value is then used as part of the communication access protocol for that specific session.

An optional address field 312 is utilized to provide additional addressing capability for memory access at the individual byte level. A data field 314 contains information such as number of retries prior to proximity test failure or success. Two cyclical redundancy fields 316 and 318 enable cyclical redundancy checks as is well known in the art.

Figure 8:
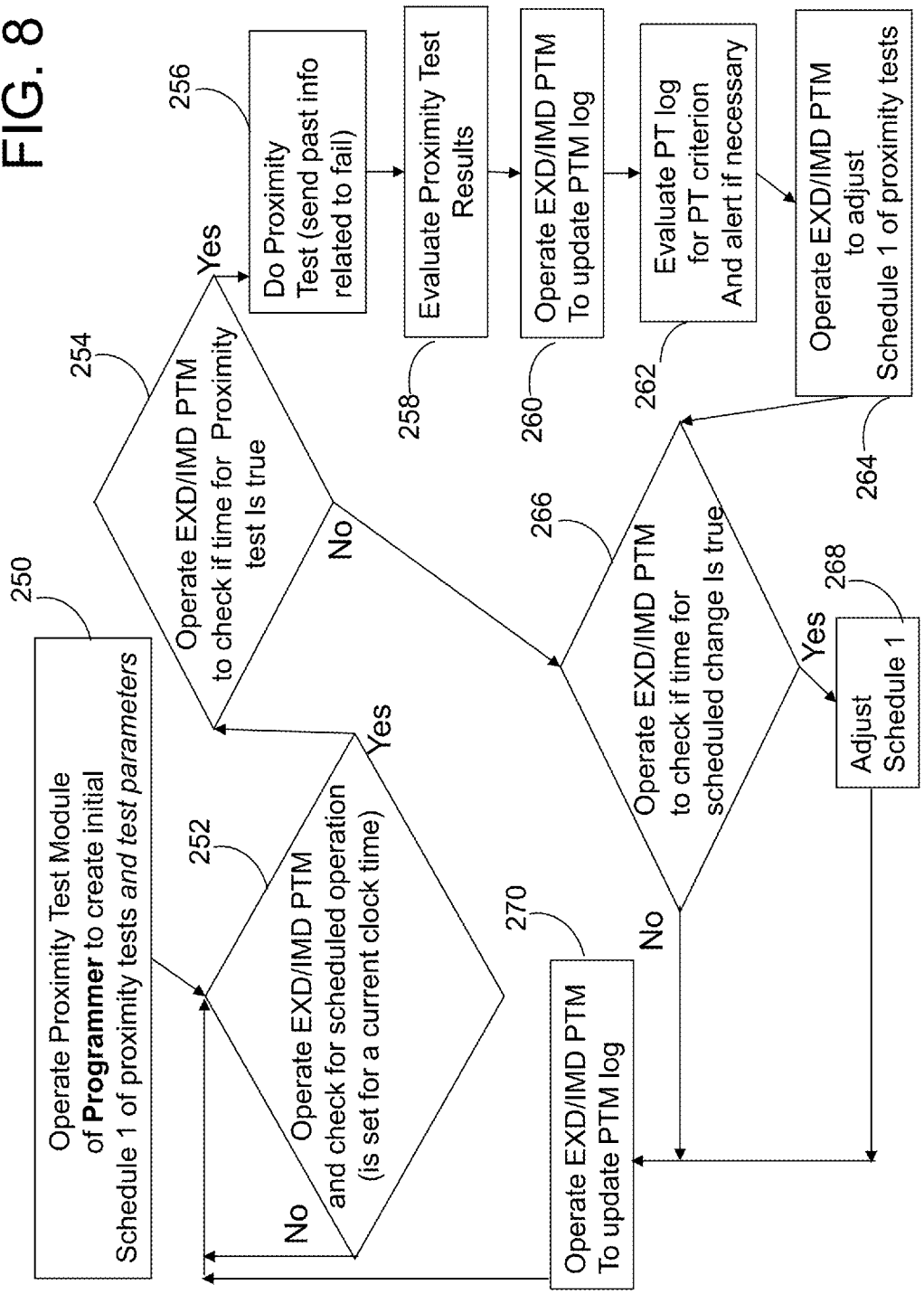
FIG. 8 is a flow chart of a method for adjusting the schedule of proximity testing.

FIG. 8 shows how proximity tests can occur according to a schedule and this schedule can change over time. The physician's programmer 64 can be used to program the system components (e.g., IMD 5, and EXD 60) in order to run the proximity tests according to a schedule. "Initial Schedule 1" for proximity tests is loaded into proximity tests modules (PTM) 66 and 477 in step 250. For example, the schedule can decrease over time where the proximity tests can occur at least 4 times per day at the start of the selected period and this can decrease to once a day or less over a selected interval. In this manner, the tests can be run more frequently for a new patient who is not accustomed to carrying around the EXD 60, and subsequently decrease over time, according to a schedule that can be contingent upon the patient successfully keeping the EXD 60 within range so that the proximity tests pass. In other words, a decrease in proximity testing may be contingently set so that the decrease only occurs if the proximity testing results indicate that the patient is keeping the EXD 60 within range. Conversely, an increased number of proximity tests may be scheduled in the case where proximity tests fail. In a first example of a schedule changing over time, at least one device (which may be the IMD 5, EXD 60, or both) causes its CPU to operate the PTM 66/477 in order to determine, in step 252, if a scheduled proximity test operation matches a current clock time, and if so step 254 occurs, while if not then step 252 is repeated (or is repeated after a delay). In step 254, the current clock time is checked to determine whether a proximity test is scheduled. If not, then control passes to step 266 where the PTM 66/477 is checked to see if a schedule change in PTM 66/477 testing is warranted (e.g. decreasing frequency of testing from 4× per day to 2× per day). If so, control passes to step 268, where the schedule for proximity testing is adjusted and the next time for a proximity test operation is set for the proximity test parameters in the PT modules 66/477. The proximity test log memory 64,476 is updated in step 270, and control passes back to step 252. Step 252 compares the current clock time to times of the newly scheduled operations. In this case, in order for a step such as 254 or 256 to occur, the clock time will need to match the times of the newly scheduled operations (which were updated in step 268) and which are stored in the proximity test modules 66, 477. Further, in step 266, if the current clock time does match a time defined for a schedule change to occur then control simply passes from step 266 to 270, prior to returning control to step 252.

In a second example, the proximity test results are used to adjust the schedule of proximity testing (either alone or in combination with a pre-defined schedule that changes over time) as is shown in steps 256-266 of FIG. 8. In step 256 at least one device (e.g., the IMD 5) of the system initiates the proximity test by sending out a plurality of proximity test signals and attempting to receive an ACK signal from the other device (e.g., the EXD 60). Step 256, in which proximity test signals and ACKS are sent and sought, may use at least a portion of the steps shown in FIGS. 4 and 5 to achieve an embodiment of the IMD 5 and EXD 60 proximity test. In step 256 part of the proximity test signals which are sent may include information about prior proximity test results in order to keep the IMD 5 and the EXD 60 up to date with proximity test results. For example, the IMD 5 may include prior test result information in the proximity test signal which it sends out to notify the EXD 60 that during the last proximity test it never received the ACK response it was expecting from the EXD 60 (i.e. it would send the time of a ACK-receive failure which would correspond to the last proximity test). The proximity test results are then evaluated in step 258 in order to determine if the proximity test passed or failed as well as the characteristics of the test (e.g. how long occurred between sending proximity tests signals and receiving an ACK response). The proximity test result can be a simple pass/fail result or it may be quantitative and contain, for example, the strength of the signal which was received. A quantitative value, which can be related to the quality of the communication signal (e.g., number of drops which occurred when sending a data string, summary statistics such as the variance of signal strength during the communication), may also be defined.

Next, control passes to step 260 where at least one of the proximity test logs 64, 476 are updated. In step 262, the proximity test logs are then evaluated in relation to a proximity test criterion to determine if patient alerting is necessary. When the IMD 5 is configured to provide an alert signal in response to proximity test failures, the form of the alert may be either a sonic alert signal or a vibration alert signal or both. The EXD 60 can also be configured to provide an alert signal to indicate that a series of proximity test failures have occurred (e.g. 50% of communications are failures). In order to conserve IMD 5 battery power, this may be scheduled to occur prior to (e.g. 2 days) a time when the IMD 5 is scheduled to provide a proximity failure alert. In this manner the patient may push a button on the EXD 60 to acknowledge this failure (and this can cancel the IMD 5 from providing its alert in the future). However, in the case where the EXD 60 isn't working correctly and doesn't provide an alert (e.g., it has run out of battery power), then the IMD 5 provides alerting to the patient so that the problem can be solved.

In step 262 the IMD 5 and EXD 60 can be configured to issue a See Doctor alarm if calculations, done upon the log of proximity test results, indicate a proximity test criterion has failed and this failure has been defined as an event for which the patient is alerted. Alternatively/additionally, the EXD 60 can display a text message relating to the nature of the proximity test results. An example of a proximity test criterion could be that at least 80% of the tests over a 1 month interval must result in proximity tests pass in order for an alert not to be issued. Further, the EXD 60 can be configured to contact a central station if calculations indicate a second defined proximity test criterion has failed (e.g. less than 50% pass rate) and this failure has been defined as a proximity test event for which such contacting occurs.

Control then passes to step 264 where the Schedule 1 of proximity testing may be adjusted. For example, if the last W proximity tests have passed or failed, then the frequency of proximity testing may decrease or increase, respectively. Alternatively, step 264 may operate in conjunction with step 266. Together these two steps will use "and logic" so that if step 266 is evaluated as true, and there is a scheduled change for proximity testing, then this change will only occur if step 264 also sets a flag to true. This latter flag would typically serve to indicate that a selected number or proportion of past proximity tests have not resulted in a proximity test failure condition.

It should be noted that the EXD 60 can also be configured to emit a proximity test pass alert signal when the proximity test is successful. For example, each morning at 8 a.m. the EXD 60 can perform a proximity test and can provide a green blinking light and a particular sound (or series of tones which are positive) if the proximity test was successful and a red blinking light and different sounds if the proximity test was a failure. The communication pass/failure alert signal can be selected to be at least one of auditory, vibratory, or visual. In this manner the patient can also be rewarded for keeping the EXD 60 within range rather than only being notified when there is a failure to do so.

From the perspective of the IMD 5 it is not known if the EXD 60 received the proximity test signals which were sent by the IMD 5, or if the EXD 60 replied with an ACK test signal unless the ACK is received by the IMD 5. If this does not occur then this may be due to the IMD 5 failing to send the proximity test signals, EXD 60 failing to successfully receive the proximity test signals, or may be due to the IMD 5 failing to receive ACKnowledgement. This information may be combined in different manners to obtain a more complete picture of what occurred during a proximity test. As suggested, in one embodiment when communication failures are registered either by the EXD 60 or IMD 5 then during the next successful proximity test, or other type of communication between the IMD 5 and EXD 60, the information about proximity test failures is sent between the devices so that at least one of the devices, preferably the EXD 60, contains a full log of proximity test results. However, this strategy requires energy and memory resources of the IMD 5 and EXD 60, so other approaches may offer advantages. For example, the logs of the EXD 60 and IMD 5 can be uploaded into a physician programmer 68 during patients' visits to their doctors (or during a remote session in which information is obtained in the patient's home and sent to a remote medical facility or doctor's office).

The physician programmer 68 has a proximity test module 130 which is able to download and then combine information from the IMD 5 and EXD 60 proximity test logs 64, 476. It is further configured to perform analysis on the log data to help a medical technician determine the nature of a communication failures. For example, instead of the proximity test simply being used to provide a pass or fail result (e.g., suggesting that the patient is not keeping the EXD 60 sufficiently close), the type of failure can be determined, such as failures which are often/always are due to the IMD 5 not receiving ACK-signals. In this case, if the EXD 60 is receiving communication successfully, then the problem may be with the transmission circuitry of the EXD 60 or receiving circuitry of the IMD 5.

As is shown in FIG. 9 the proximity test module 130 is designed to allow the physician programmer 68 to display the proximity test results graphically to a user. Screen component 280 shows an example of communication events for the IMD 5 (top) and EXD 60 (bottom) in which proximity test signals are sent (S), and acknowledged (ACK). The component 280 shows that the proximity test starts with the IMD 5 sending a signal, a slight time later the EXD 60 receives the signal with a strength of 5 to which it responds (ACK5), where strength of 5 is a very strong signal and 1 is a very weak signal. The IMD 5 receives this ACK with a strength of 2 a short time later (ACK2). The next time the IMD 5 sends a proximity test signal, the EXD 60 does not receive it and so it does not send an ACK back. The IMD 5 waits a defined period of time and then creates a fail response (ACKF) indicating the proximity test failed. In the final proximity test operation which is shown, the IMD 5 sends a proximity test signal and the EXD 60 receives the signal with a strength of 4 to which it responds (ACK4), and the IMD 5 then receives this ACK with a strength of 3 a short time later (ACK3). The user can click on any of the items displayed by screen component 280 and obtain the rest of the details about the event (e.g., time of event, number of retries prior to a signal being received). The users can also right-click on the image to open up a table with all the proximity test events and their corresponding parameters. In this example, while the IMD 5 seems to obtain the ACK signals sent from the EXD 60, the EXD 60 seems to receive signals sent from the IMD 5 with low strength or does not receive the signals successfully at all.

The programmer's proximity test module is further configured to calculate, with these proximity test results, and provide a proximity test result profile which is displayed as screen component 282. In this example, values A-H show summary statistics which are calculated upon the proximity test results. For example, "A" shows the average time (in seconds) required for the EXD 60 to respond after the IMD 5 sends a proximity test signal.

The physician programmer can also provide customization for what occurs during proximity testing. The "change send duration" option 284 allows the duration for which proximity test signals are sent to be modified. The "change send strength" option 286 allows the strength with which proximity test signals are sent to be modified, either by increasing the power of transmission or a protocol which uses more than one transmission frequency. Although this may use more power in the IMD 5, it may be needed in cases where communication errors are occurring. The "change # send" option 288 can be used to change the number of sent proximity test signal retries when no ACK is obtained (e.g. the retry-ctr proximity test parameter value of step 100 in FIG. 4). The "change ACK wait duration/#" option 290 can be used to change the duration that the device will wait to receive test signals and the number of retries which occur when no ACK is obtained (e.g. the T proximity test parameter value of step 108 in FIG. 4, and TH value of step 160 of FIG. 5). The "change proximity test fail operations" option 292 can be used to change the response when a number (G) of proximity tests fail such as whether the IMD 5 or EXD 60 or both issue an alert signal due to this failure. The "change EXD 60/ACC" option 294 is used to determine how and if the EXD 60 and proximity test accessory (134 of FIG. 1) are used during the proximity tests. For example, the EXD 60 can be programmed to perform proximity tests with the accessory 134 rather than the IMD 5 so that the IMD 5 doesn't un-necessarily use up its internal power source during initial training of a patient when multiple proximity tests can occur in the same day.

Figure 10:
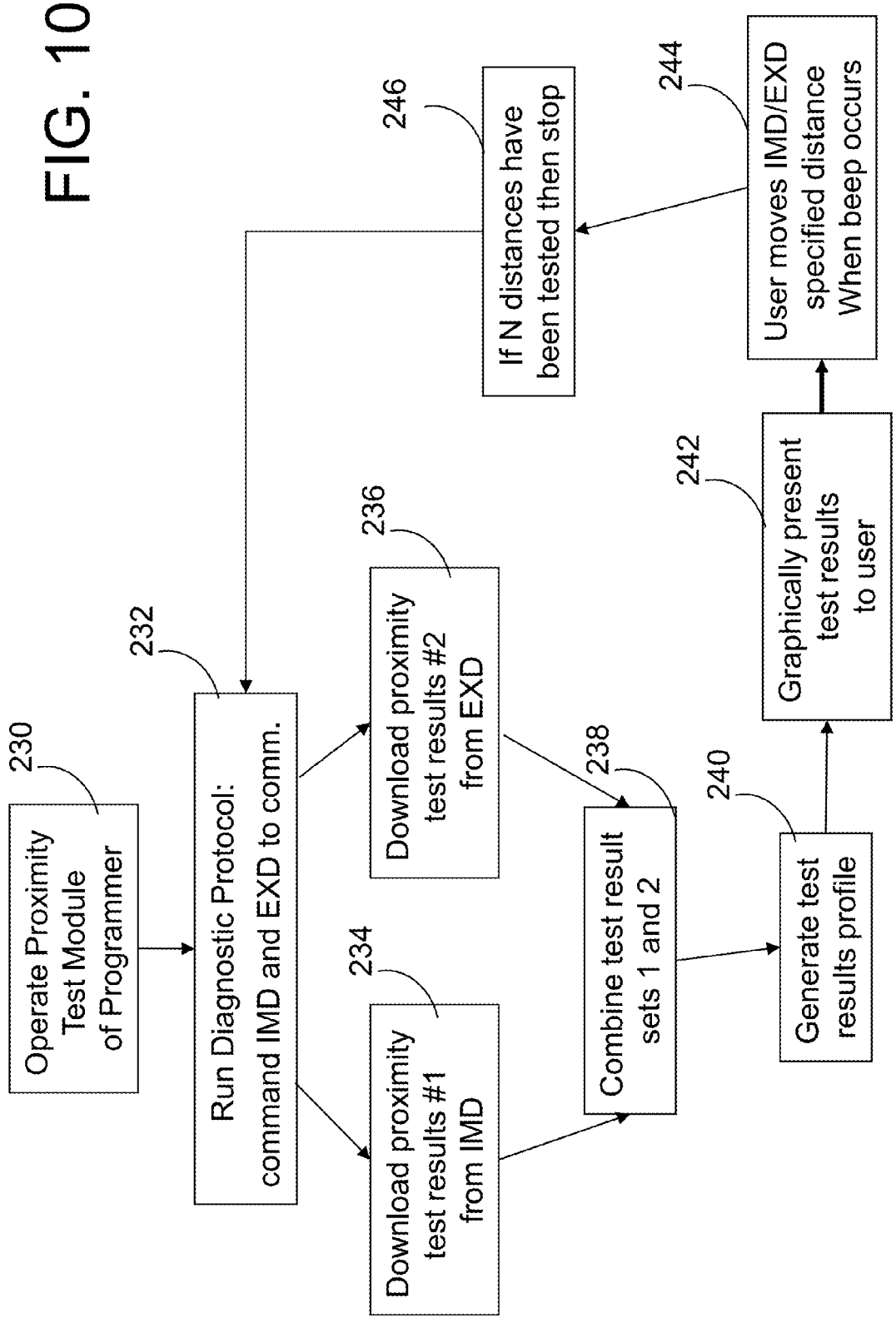
FIG. 10 is a flow chart of a method for performing a diagnostic proximity test by a medical technician.

In cases where there are proximity test failures, additional testing may be necessary during a doctor visit in order to assist with determining the source of the problem. The programmer is configured with a "run proximity test" option 296 which allows an operator to run a diagnostic protocol. For example, the diagnostic test protocol may include a method of FIG. 10 in which the step of operating the proximity test module of the programmer 230 includes selecting the "run proximity test" option 296 (of FIG. 9) in order to initiate the step of running the diagnostic protocol 232. Step 232 can include the initiation of a communication session between the programmer, the IMD 5 and the EXD 60. This step 232 then passes control to steps 234-236, where a download of the proximity test results from the IMD 5 and EXD 60 occurs. In step 238, the test results from the IMD 5 (set #1) and the EXD 60 (set #2) are combined and the test results profile is created 240 and displayed 242 as is shown in screen component 282. In the example given, the diagnostic protocol is selected, which causes the programmer to perform a series of proximity tests in which the patient or operator are instructed to move the EXD 60 1 foot further away from the patient each time the programmer emits a beep. After this, control passes back to step 232 so that communication can be assessed at the several instructed distances. This occurs until step 246 indicates that all the intended distances have been evaluated, which causes the test to stop.

The various parameters of the proximity test protocol which occur regularly at home can be programmably adjusted using the "Set proximity home-based test parameters/schedule" 298, which allows the operator to adjust the characteristics of the tests that occur at home.

Some of the steps in figures can occur earlier or later than are shown, steps can also be repeated, and steps may also be omitted altogether. The steps of the particular methods shown here can be incorporated into variants of other methods which are shown. Various other modifications, adaptations, and alternative designs are of course possible in light of the above teachings. Therefore, it should be understood at this time that, within the scope of the appended claims, the invention can be practiced otherwise than as specifically described herein.

We claim:

1. A medical device system, the system comprising:
   an implanted medical device, and
   an external device comprising a transceiver, a random access memory, and a processor coupled to the transceiver and the random access memory, wherein the processor is configured to:
   periodically activate wireless communication circuitry in an attempt to communicate a plurality of proximity test signals with the implanted medical device;

for each of the plurality of activations, determine whether a proximity signal has been received from the implanted device within a certain time after the activation, thereby generating a plurality of proximity test receipt results;

apply a test to the plurality of proximity test receipt results to determine whether a proximity failure condition exists, thereby generating a plurality of proximity test results;

operative when a proximity failure condition exists, take at least one of the following actions: store information regarding the proximity failure in the random access memory or send a proximity test failure condition notification; and when the proximity failures in the random access memory meet a selected first proximity test criterion, the processor is further configured to send notification to the patient.

2. The medical device system according to claim 1 wherein the processor is further configured to send notification to a remote station when the proximity failures in the random access memory meet a selected second proximity test criterion.

3. The medical device system according to claim 1 wherein the periodic activation occurs every 24 hours.

4. The medical device system of claim 1 further including a proximity test module which operates upon the random access memory to provide a log of the plurality of proximity test results including a time of each test and a quantitative value related to a strength of each of the plurality of the proximity test signals.

5. The medical device system of claim 1 further including a proximity test module which operates upon the random access memory to provide a log of the plurality of proximity test results including a time of each test and a qualitative value related to a quality of each of the plurality of the proximity test signals.

6. The medical device system of claim 1 wherein the implantable medical device is configured to provide a proximity test in conjunction with the external device and to derive and store a second plurality of proximity test results.

7. The medical device system of claim 6 further including a programmer device configured for downloading the second plurality of proximity test results from the implanted device and processing these test results to provide a test result profile.

8. The medical device system of claim 6 further including a programmer device configured for downloading the second plurality of proximity test results from the implanted device and presenting the test results graphically to a user.

9. The medical device system of claim 6 further including a programmer configured for running a diagnostic protocol which causes at least one of the implanted device and external device to perform selected proximity tests according to a diagnostic protocol, and to evaluate the second plurality of proximity test results.

10. The medical device system of claim 6 further including a programmer device configured for downloading the second plurality of proximity test results of the implanted device and presenting the test results graphically to a user.

11. The medical device system of claim 1 further including a programmer device configured for downloading the plurality of proximity test results of the external device and processing these test results to provide a test result profile.

12. The medical device system of claim 1 further including a programmer configured for running a diagnostic protocol which causes the external device to perform selected proximity tests according to a diagnostic protocol, and to evaluate the plurality of proximity test results.

13. The medical device system of claim 1 further including a programmer configured for running a diagnostic protocol which causes the external device to perform selected proximity tests according to a diagnostic protocol, and to display the plurality of proximity test results.

14. The medical device system of claim 1 wherein the periodic activation of the wireless communication circuitry in an attempt to communicate a plurality of proximity test signals with the implanted medical device, includes operating the wireless communication circuitry to receive a plurality of proximity test signals transmitted by the implanted medical device.

15. The medical device system of claim 1 wherein the periodic activation of the wireless communication circuitry in an attempt to communicate a plurality of proximity test signals with the implanted medical device, includes operating the wireless communication circuitry to send a plurality of proximity test signals which are designed to be received by the implanted medical device.

16. The medical device system according to claim 1 wherein the periodic activation occurs as a function of the plurality of proximity test results so that the plurality of proximity test results are used to adjust the schedule of proximity testing.

17. The medical device system according to claim 1 wherein the periodic activation occurs as a function of the plurality of proximity test results.

18. The medical device system according to claim 1 wherein the periodic activation occurs as a function of the plurality of proximity test results and according to a programmable schedule that decreases when the communication tests are successful, thereby indicating patient compliance in keeping the external device sufficiently close to the patient wherein the tests are successful.

19. A medical device system, the system comprising:
an implanted medical device, and
an external device comprising a transceiver, a random access memory, and a processor coupled to the transceiver and the random access memory, wherein the processor is configured to:
periodically activate wireless communication circuitry in an attempt to communicate a plurality of proximity test signals with the implanted medical device;
for each of the plurality of activations, determine whether a proximity signal has been received from the implanted device within a certain time after the activation, thereby generating a plurality of proximity test receipt results;
apply a test to the plurality of proximity test receipt results to determine whether a proximity failure condition exists, thereby generating a plurality of proximity test results;
operative when a proximity failure condition exists, take at least one of the following actions: store information regarding the proximity failure in the random access memory or send a proximity test failure condition notification; and
when the proximity failures in the random access memory meet a selected proximity test criterion, the processor is further configured to send notification to a remote station.

20. A medical device system, the system comprising:
an implanted medical device, and an external device comprising a transceiver, a random access memory, and a processor coupled to the transceiver and the random access memory, wherein the processor is configured to:

periodically activate wireless communication circuitry to transmit a plurality of proximity test signals with the implanted medical device;

when the external device receives an acknowledge signal from said implanted medical device responsive to at least one proximity test signal, the processor stores the acknowledge signal and generates a proximity test receipt result indicating that both the proximity test signal and the acknowledgement signal were received;

when the external device does not receive an acknowledge signal from said implanted medical device responsive to at least one proximity test signal, the processor is further configured to store the proximity test signal and generate a proximity test receipt result indicating that there was no acknowledge signal sent from the implanted medical device defining a proximity failure; and, when a plurality of proximity failures stored in the random access memory meets a selected proximity test criteria, the processor is further configured to document said test receipt results, whereby a patient or caregiver is notified as to compliance or non-compliance of the patient with maintaining the implanted medical device within a predetermined proximity of the external device.

* * * * *